(12) United States Patent
Takio et al.

(10) Patent No.: US 8,815,898 B2
(45) Date of Patent: Aug. 26, 2014

(54) 6,7-DISUBSTITUTED-SIOQUINOLINE DERIVATIVES AND THEIR USE

(75) Inventors: Ville Takio, Lokalahti (FI); Matti Ekholm, Kuopio (FI)

(73) Assignee: Montisera Ltd, Turku (FI)

( * ) Notice: Subject to any disclaimer, the term of this patent is extended or adjusted under 35 U.S.C. 154(b) by 0 days.

(21) Appl. No.: 13/814,987

(22) PCT Filed: Aug. 10, 2011

(86) PCT No.: PCT/FI2011/050707
§ 371 (c)(1),
(2), (4) Date: Feb. 8, 2013

(87) PCT Pub. No.: WO2012/020170
PCT Pub. Date: Feb. 16, 2012

(65) Prior Publication Data
US 2013/0137719 A1    May 30, 2013

(30) Foreign Application Priority Data
Aug. 11, 2010 (EP) ..................................... 10397511

(51) Int. Cl.
C07D 217/02 (2006.01)
A61K 31/472 (2006.01)
C07D 217/22 (2006.01)

(52) U.S. Cl.
CPC ............ C07D 217/02 (2013.01); C07D 217/22 (2013.01); A61K 31/472 (2013.01)
USPC .......................................... 514/307; 546/139

(58) Field of Classification Search
None
See application file for complete search history.

(56) References Cited

FOREIGN PATENT DOCUMENTS

EP     2090576 A1 *  8/2009
JP     3 148222 A    6/1991

OTHER PUBLICATIONS

Wu et al., Toxicology, 236, pp. 1-6, 2007.*
PCT International Search Report and Written Opinion; PCT/FI2011/050707; Jan. 12, 2012.
Saitoh, T., et al; "Synthesis and in vitro cytotoxicity of 1,2,3,4-testrahydroisoquinoline derivatives", European Journal of Medicinal Chemistry Editions Scientifique Elsevier, Paris, FR, vol. 41, No. 2, Feb. 1, 2006, pp. 241-252, XP024993836.
Okuda Katsuhito et al; "Parkinsonism-preventing activity of 1-methyl-1,2,3,4-tetrahydroisoqui noline derivatives in C57BL mouse in vivo", Biological & Pharfmaceutical Bulletin, vol. 29, No. 7, Jul. 2006, pp. 1401-1403, XP002632499.
Database accession No. 1342184-32-0; Database Registry (Online) Chemical Abstracts Service, Columbus, Ohio, US; Nov. 7, 2011, XP002666855, retrieved from STN accession No. 1342184-32-0.

* cited by examiner

Primary Examiner — Zinna Northington Davis
(74) Attorney, Agent, or Firm — Gearhart Law, LLC

(57) ABSTRACT

The present invention relates compounds of general formula (I) and stereoisomers and pharmaceutically acceptable salts and prodrugs thereof; wherein R' and $R_1$-$R_5$ are as defined in the claims. The invention also relates to said compounds for use as a medicament and particularly in the treatment of drug addiction and CNS related diseases.

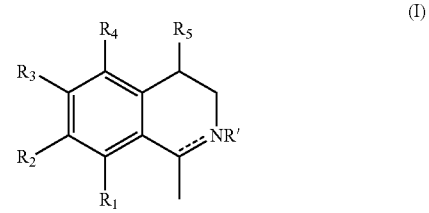

(I)

11 Claims, No Drawings

6,7-DISUBSTITUTED-SIOQUINOLINE DERIVATIVES AND THEIR USE

CONTINUING DATA

This application is a 371 of PCT/FI2011/050707 filed Aug. 10, 2011.

FIELD OF THE INVENTION

The present invention relates to novel 6,7-disubstituted-isoquinoline derivatives and more particularly to novel 6,7-disubstituted-1-methyl-1,2,3,4-tetrahydro- and -3,4-dihydroisoquinoline derivatives and pharmaceutical compositions comprising them. The invention also relates to said compounds for use in the treatment of drug addiction and CNS related diseases.

BACKGROUND OF THE INVENTION

Endogenous isoquinolines are formed by condensation of biogenic amines—such as phenethylamine—and simple aldehydes, such as formaldehyde or acetaldehyde. They are known to modulate neurotransmission, central metabolism and motor activity. An endogenous TIQ derivative salsolinol (1-methyl-1,2,3,4-tetrahydroisoquinoline-6,7-diol) is considered to be a causative factor of Parkinson's disease (PD), while (R)-1-MeTIQ (1-methyl-1,2,3,4-tetrahydroisoquinoline) was shown to possess an antiparkinsonian activity. Until recently 1MeTIQ was the only known neuroprotective/PD preventing TIQ derivative. In 2006 Katsuhiro OKUDA et al. (Biological and Pharmaceutical Bulletin 29 (2006) pp. 1401-1403) discovered that 5-/6-/7-monohydroxylated 1MeTIQ derivatives are neuroprotective and PD preventing indeed, even more so than the parent compound.

It has been demonstrated that concentrations of many endogenous TIQ derivatives are significantly elevated in the urine and cerebrospinal fluid of PD/ADHD (attention deficit hyperactivity disorder) patients compared to controls, the content of 1MeTIQ however is significantly decreased in PD patients' cerebrospinal fluid and brain.

Salsolinol is formed enzymatically as well as non-enzymatically as a condensation product of acetaldehyde—the primary metabolite of ethanol—with dopamine in the brain of mammals. Salsolinol affects the uptake of catecholamines into nerve terminals, the release of stored catecholamines and the activity of monoamine oxidase (MAO), catechol-O-methyl transferase (COMT) and tyrosine hydroxylase. Ethanol induced elevation of salsolinol levels is known to participate in the development of ethanol addiction/alcoholism.

Salsolinol (SAL) has been postulated to mediate some of the addictive properties of alcohol. A number of studies have shown that primates self-administer SAL even in nanomolar concentrations when intracranially injected to certain brain region. Also acetaldehyde is self-administered when injected intracranially although much higher concentrations are needed. Studies have confirmed that SAL is released during suckling on lactating sheep. It is clear that SAL mediates reinforcing effects on a number of primate species. Studies have shown that controlled amounts of ethanol intake have only miniscule effect on brain SAL levels. Still it is clear that ethanol intake elevates dopamine and acetaldehyde concentrations inside brain and so the concentrations of starting materials for Pictet-Spengler reaction forming SAL are elevated. In this light it seems certain that alcoholics with higher ethanol intake and generally higher aldehyde dehydrogenase (ALDH) activity (see Alcohol Clin. Exp. Res. 2009 November; 33 (11):1935-44) try to compensate lower acetaldehyde and SAL concentrations by increased drinking.

Most tetrahydroisoquinolines penetrate to the brain in pharmacologically relevant amounts and induce a variety of effects. Most of the TIQ and 1MeTIQ exit the brain (90.4% and 95.3%) and is excreted in urine (76% and 72%) unchanged. The hydroxylated (C4 of the isoquinoline backbone) derivatives of TIQ and 1MeTIQ were the most abundant metabolites in the urine (2.7% 8.7%).

In European Journal of Medicinal Chemistry 41 (2006) pp. 241-252 6-fluoro-1-methyl-1,2,3,4-tetrahydroisoquinoline has been reported as a possible agent against Parkinson's disease.

EP 2 090 576 A1 discloses certain 5,8- and 6,7-difluoro substituted isoquinolines as intermediates in the preparation of pyrazolo[1,5-a]pyridines for use as metabotropic glutamate receptor modulators.

It has now surprisingly been found that the substitution of 6- and 7-positions of the isoquinoline backbone blocks the adverse metabolic formation of dihydroxy compounds and thereby also improves the desired activity of the isoquinoline compound in question.

SUMMARY OF THE INVENTION

The present invention relates to novel compounds of general formula (I)

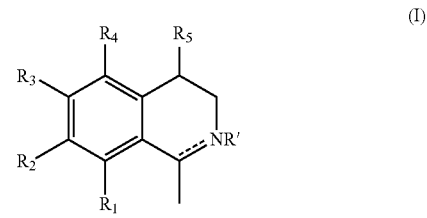

and stereoisomers and pharmaceutically acceptable salts and prodrugs thereof;
wherein the dotted line represents an optional bond;
R' is H, or
R' is absent, when the dotted line represent a bond;
$R_1$ and $R_4$ are each independently selected from the group consisting of H, halo, lower alkyl, trifluoromethyl and trifluoromethoxy;
$R_2$ and $R_3$ are both F, or one of $R_2$ and $R_3$ is F and the other is lower alkyl or trifluoromethyl; and
$R_5$ is selected from the group consisting of halo, lower alkyl, trifluoromethyl and trifluoromethoxy, or when the dotted line represents a bond, and then $R_5$ may also be H.

The invention also relates to a pharmaceutical composition comprising an effective amount of one or more compounds of formula (I) or stereoisomers or pharmaceutical acceptable salts thereof and a pharmaceutically acceptable carrier and suitable excipients.

Further, the invention relates to compounds of formula (I) or stereoisomers or pharmaceutically acceptable salts thereof for use as a medicament.

The invention also relates to compounds of formula (I) or stereoisomers or pharmaceutically acceptable salts thereof for use in the treatment of drug addiction, alcoholism, anorexia, bulimia, and CNS related diseases.

DETAILED DESCRIPTION OF THE INVENTION

In the definition of the compound group of formula (I) according to the invention the term "halo" refers to F, Cl, I and Br, preferably F. By the term "lower alkyl" is meant saturated branched or linear hydrocarbons containing 1-6 carbon atoms, preferably 1-3 carbon atoms, especially methyl or ethyl.

Examples of preferred compounds of formula (I) are those where the dotted line represents a bond. Among these compounds preferred compounds are those where $R_1$, $R_2$ and $R_3$ are H. Further preferred compounds are those where $R_1$ and $R_2$ are H and $R_3$ is F or methyl. Preferred specific compounds are
6,7-difluoro-1-methyl-3,4-dihydroisoquinoline,
1-methyl-4,6,7-trifluoro-3,4-dihydroisoquinoline,
4,6,7-trifuoro-1-methyl-1,2,3,4-tetrahydroisoquinoline,
4,6-difluoro-1,7-dimethyl-3,4-dihydroisoquinoline, and pharmaceutically acceptable salts and prodrugs thereof.

Typical pharmaceutically acceptable salts are acid addition salts formed with inorganic acids, such as hydrochloric acid, hydrobromic acid, sulfuric acid, phosphoric acid, nitric acid, and the like, and salts formed with organic acids, such as acetic acid, oxalic acid, tartaric acid, succinic acid, malic acid, fumaric acid, maleic acid, ascorbic acid, benzoic acid and the like. Pharmaceutically acceptable salts also include alkali metal salts, (e.g. sodium and potassium), alkaline earth metal salts (e.g. calcium or magnesium), aluminium salts, ammonium salts and salts with organic amines such as with methylamine, dimethylamine, trimethylamine, ethylamine, triethylamine, morpholine, and the like.

Pharmaceutical compositions comprising one or more compounds of the invention may further contain conventional carriers, diluents or excipients and may be administered in a solid dosage form, such as tablets or capsules, or in a liquid form, such as solutions, suspensions, emulsions, elixirs, for oral use, or in the form of sterile injectable solutions for parenteral use.

Solid dosage forms may additionally include, e.g., binders, such as microcrystalline cellulose, gum tragacanth or gelatine; excipients, such as starch or lactose, disintegrating agent, such as alginic acid or corn starch; lubricants, such as magnesium stearate; glidants, such as colloidal silicon dioxide; and sweeteners and flavoring agents and like. Liquid dosage forms suitable for oral administration may include a suitable aqueous or non-aqueous vehicle with buffers, suspending and dispensing agents, colorants, flavors and the like. For parenteral use, compositions are formed in sterile saline or phosphate buffered saline or other injectable vehicles known in the art.

Such pharmaceutical compositions and dosage forms contain a compound of the invention in an amount effective for the desired purpose. The effective amount will typically be determined by a physician, and depend on the condition to be treated, the chosen route of administration, the actual compound administered, the age, weight, and response of the individual patient, the severity of the patient's symptoms, and like.

Endogenous isoquinolines are compounds which are formed by condensation of biogenic amines and simple aldehydes such as formaldehyde or acetaldehyde. The compounds of the invention can be synthesized using well documented reactions and commercially available starting materials. We have explored a series of new TIQ derivatives primarily targeted to mimic the actions of 1MeTIQ and also SAL to some extent. These novel 1MeTIQ compounds can be used to achieve many desirable pharmacological responses. Fluorination can alter the bond strength, lipophilicity, conformation, electrostatic potential, dipoles, and pKa.

Substitution, especially fluorination, at the position of metabolic attack—mainly at positions 6, 7 and 4—is used to alter the route and rate of metabolic degradation. Fluorination may also alter the tissue distribution, pharmacodynamics and toxicology of the compound. It can be generalized that replacing hydrogen with fluorine causes minimal steric effects at the receptor.

By replacing both of the catechol hydroxyls of SAL, especially with fluorine, a better targeting of the drug distribution and smaller active dosages are achieved. Unlike SAL, the compounds of the present invention are actively transported over the blood brain barrier by organic cation transporters and are concentrated in the brain. Most of the compounds of the present invention cannot be oxidized to form epoxides thereby making them less prone to cause oxidative stress. The compounds of the invention are associated with neuroprotective and neuroregenerative properties instead of neurotoxicity or neurodegeneration, which is the case with SAL. Further, the novel compounds are better in mimicking desirable effects of SAL and treating alcoholism and Parkinson's disease than e.g. 6-monofluorinated TIQ.

The novel compounds according to the invention are structurally related to 1MeTIQ. Thus, the novel compounds can be used, in addition to the treatment of e.g. Alzheimer's disease and Parkinson's disease, to treat addictions in general—from alcohol to cocaine and heroin. Number of positive pharmacological responses can be achieved simultaneously. While decreasing the tendency to relapse and likelihood of developing an addiction, these compounds can act as general mood stabilizers and general neuroprotectants possessing remarkable antiparkinsonian and antiepileptic character.

The compounds exhibit many pharmacological responses, such as
   prolonging the duration of morphine without enhancing the peak action
   antagonizing the development of morphine tolerance
   reducing the naloxone-precipitated withdrawal symptoms
   inhibiting the reinstatement of cocaine self-administration
   attenuating cravings
   inhibiting the activity of monoamine-oxidases (MAOs)
   inhibiting the activity of acetylcholinesterase (ACE)
   neuroprotection
   shifting the catabolism of catecholamine neurotransmitters towards catechol-O-methyl transferase (COMT)-dependent methylation
   inhibition or enhancement of the release of prolactin
   releasing norepinephrine
   inducing or inhibiting neuron related apoptosis and/or necrosis
   abolishing cocaine induced inhibition of noradrenalin metabolism.

The compounds according to the present invention may be prepared by processes known per se as follows.

Step 1. Knoevenagel Condensation—Tet. Lett. 39, 8013-8016 (1998):

1.0 mol eq. subst. benzaldehyde, 1.2 mol eq. nitromethane, 0.47 mol eq. ammonium acetate and 0.35 mol eq. glacial acetic acid (GAA) was sonicated (40 kHz) at RT for 3 h. After removal of nitromethane, partition between dichloromethane and water then brine gave a crude product which was recrystallized from aq, (m)ethanol or AcOH; or 1.0 mol eq. subst. benzaldehyde, 1.2 mol eq. nitromethane and 0.1 mol eq. cyclohexylamine was mixed and kept in dark for 4 weeks, or until $H_2O$ formation ceased. The crude product was ground, washed with brine and recrystallized from aq. (m)ethanol or AcOH; or in the case of $R_5$ halogen substitution (preferably fluorine), the synthesis proceeds via nitroalcohol intermediate, otherwise skip to step 4:

1.0 mol eq. subst. benzaldehyde, with 1.0 mol eq. of triethylamine and 1.2 mol eq. nitromethane was stirred in methanol at −12° C. for 2½ h, and the amine quenched with 1.0 mol eq. of GAA while still freezing cold. Most of the solvent was stripped under vacuum, and the remains were dissolved in dichloromethane (DCM) and washed two times with water and once with brine. The DCM was stripped, leaving behind the crude nitroalcohol.

Step 2. (in the case of $R_5$ halogen substitution) Sulfonating the aliphatic OH-group to appropriate sulfonyl ester by stirring 1.0 mol eq. of subst. phenyl-2-amine-1-ol in DCM with 1.2 mol eq. of triethylamine (or using pyridine for the solvent) with and adding slowly 1.1 mol eq. of methylsulfonyl chloride maintaining the temperature at −5° C. until conversion was complete. The product was washed several times with brine, dried over anhydrous $MgSO_4$ and concentrated in vacuo.

Step 3. (in the case of $R_5$ halogen substitution) Modified Finkelstein reaction to the sulfonate ester with potassium halide (in this case KF) proceeded by dissolving 1 mol eq. of sulfonyl-intermediate from the step 2 with 6 ml of acetonitrile per gram of substrate, 0.5 mol eq. of 1-butyl-3-methyl-imidazolium tetrafluoroborate and 5 mol eq. of $H_2O$ which after 1.05 mol eq. amount of KF was added and the solution was mixed and sonicated at RT for 180 min or until TLC showed completion. The $R_5$-halogen substituted compounds were then extracted with DCM and washed several times with brine, dried over anhydrous $MgSO_4$ and concentrated in vacuo prior proceeding.

Step 4. Reduction of the possible C=C bond and nitrogroup to the amino-group according to procedures well known in the art.

Step 5. Pictet-Spengler reaction—industrial scale (EP 0929527):

1.0 mol eq. subst. N-tosyl-phenethylamine and 3.0 mol eq. boron trifluoroetherate was refluxed with 21.0 mol eq. of 1,1-diethoxyethane for 12 h in $N_2$ atmosphere or until TLC showed completion. The nitrogen is afterwards de-protected; or 1.0 mol eq. subst. phenethylamine was refluxed for 1 h with 3.0 mol eq. acetaldehyde which after 1.2 mol eq. hydrochloric acid 37% was added and refluxing was continued until TLC showed completion.

Step 6. Workup

The reaction mixture was partitioned between ethyl acetate (10 ml/1 g substrate) and water (10 ml/1 g substrate), separated, and the organic layer was washed twice with saturated sodium bicarbonate and dried over sodium sulfate ($Na_2SO_4$). The drying agent was filtered off and the filtrate was distilled under reduced pressure to yield the desired compound.

The method of preparing 3,4-dihydroisoquinolines from 1,2,3,4-tetrahydroisoquinolines is well known and also described in U.S. Pat. No. 6,034,094.

The pharmaceutically acceptable salts of the compounds of formula (I) may be prepared by conventional processes well-known to the person skilled in the art. For the preparation of pharmaceutical compositions and dosage forms as well as the carriers, diluents and expedients used in the preparation, see, for example, Remington's Pharmaceutical Sciences, 20th Edition, 2000, Marck Publishing Company, Easton, Pa.

The pharmacological activity of the compounds of the invention can be verified by methods known in the art. For example, the reducing effect on alcohol seeking behavior can be verified using the procedure described by Heidbreder, C. A., et al., Addict Biol. 2007 March; 12 (1):35-50. The parkinsonism-preventing activity can be shown, for example, as described by Okuda, K., et al. Biol Pharm Bull. 2006 July; 29 (7):1401-1403.

The following specific non-limiting examples will further identify the compounds of the invention.

Example 1

6,7-difluoro-1-methyl-3,4-dihydroisoquinoline

1H NMR (CDCl3): δ ppm 7.450 (3, 1H, d, J=4.858), 2.277 (6, 3H), 3.647 (8, 1H, ddd, J=13.253, J=9.980, J=3.970), 3.848 (8, 1H, ddd, J=13.253, J=3.860, J=1.950), 3.019 (9, 1H, ddd, J=14.326, J=3.970, J=1.950), 2.849 (9, 1H, ddd, J=14.326, J=9.980, J=3.860), 7.260 (11, 1H, d, J=4.858). B.P. 112-116° C. at 10 mmHg.

Example 2

1-methyl-4,6,7-trifluoro-3,4-dihydroisoquinoline

1H NMR (CDCl3): δ ppm 7.493 (3, 1H, d, J=5.422), 2.238 (6, 3H), 3.886 (8, 1H, dd, J=13.927, J=3.970), 3.943 (8, 1H, dd, J=13.927, J=1.960), 5.884 (9, 1H, dd, J=3.970, J=1.960), 7.763 (12, 1H, d, J=5.422). B.P. 118-122° C. at 10 mmHg.

Example 3

4,6,7-trifluoro-1-methyl-1,2,3,4-tetrahydroisoquinoline

1H NMR (CDCl3): δ ppm 7.466 (3, 1H, d, J=5.020), 3.930 (5, 1H, q, J=6.684), 1.213 (6, 3H, d, J=6.684), 3.065 (8, 1H, dd, J=14.188, J=3.650), 3.089 (8, 1H, dd, J=14.188, J=2.050), 5.788 (9, 1H, dd, J=3.650, J=2.050), 7.602 (12, 1H, d, J=5.020). B.P. 108-113° C. at 10 mmHg.

Example 4

4,7,8-trifluoro-1-methyl-6-(trifluoromethyl)-3,4-dihydroisoquinoline

1H NMR (CDCl3): δ ppm 2.126 (1, 3H), 7.417 (8, 1H), 3.713 (9, 1H, dd, J=13.900, J=9.980), 4.072 (9, 1H, dd, J=13.900, J=3.860), 5.690 (17, 1H, dd, J=9.980, J=3.860). B.P. 133-137 at 10 mmHg.

Example 5

4,6-difluoro-1,7-dimethyl-3,4-dihydroisoquinoline

1H NMR (CDCl3): δ ppm 2.242 (1, 3H), 2.326 (2, 3H), 7.350 (5, 1H, d, J=4.325), 7.626 (6, 1H, d, J=4.325), 3.668 (7, 1H, dd, J=14.314, J=9.980), 4.011 (7, 1H, dd, J=14.314, J=3.860), 5.875 (14, 1H, dd, J=9.980, J=3.860) B.P. 135-140 at 10 mmHg.

What is claimed is:

1. A compound of formula (I)

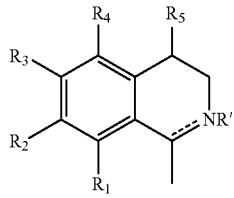

(I)

or stereoisomers or pharmaceutically acceptable salts thereof;

wherein the dotted line represents an optional bond;

R' is H, or

R' is absent, when the dotted line represent a bond;

$R_1$ and $R_4$ are each independently selected from the group consisting of H, halo, lower alkyl, trifluoromethyl and trifluoromethoxy;

$R_2$ and $R_3$ are both F, or one of $R_2$ and $R_3$ is F and the other is lower alkyl or trifluoromethyl; and $R_5$ is selected from the group consisting of halo, lower alkyl, trifluoromethyl and trifluoromethoxy, or when the dotted line represents a bond, then $R_5$ may also be H.

2. The compound of formula (I) as defined in claim 1, wherein the dotted line is a bond and $R_1$, $R_4$ and $R_5$ are H, and $R_2$ and $R_3$ are F.

3. The compound of formula (I) as defined in claim 1, wherein $R_1$ and $R_4$ are H, and $R_2$, $R_3$ and $R_5$ are F.

4. The compound of formula (I) as defined in claim 1, wherein $R_1$ and $R_4$ are H, $R_2$ and $R_3$ are F, and $R_5$ is methyl.

5. The compound of formula (I) as defined in claim 1, wherein the compound is 6,7-difluoro-1-methyl-3,4-dihydroisoquinoline or a pharmaceutically acceptable salt thereof.

6. The compound of formula (I) as defined in claim 1, wherein the compound is 1-methyl-4,6,7-trifluoro-3,4-dihydroisoquinoline or a pharmaceutically acceptable salt thereof.

7. The compound of formula (I) as defined in claim 1, wherein the compound is 4,6,7-trifluoro-1-methyl-1,2,3,4-tetrahydroisoquinoline or a pharmaceutically acceptable salt thereof.

8. A pharmaceutical composition comprising an effective amount of one or more compounds of formula (I) as defined in claim 1, or a stereoisomer or a pharmaceutically acceptable salt thereof, and a pharmaceutically acceptable carrier and suitable excipients.

9. The compound of formula (I) as defined in claim 1, or a stereoisomer or pharmaceutically acceptable salt thereof for use as a medicament.

10. The compound of formula (I) as defined in claim 1, or a stereoisomer or pharmaceutically acceptable salt thereof for use in the treatment of CNS related diseases.

11. The compound of formula (I) as defined in claim 1, or a stereoisomer or pharmaceutically acceptable salt thereof for use in the treatment of a disease selected from the group consisting of Alzheimer's disease, Parkinson's disease, depression, hyperactivity, narcolepsy and drug addiction, alcoholism, anorexia and bulimia.

* * * * *

UNITED STATES PATENT AND TRADEMARK OFFICE
CERTIFICATE OF CORRECTION

PATENT NO. : 8,815,898 B2  
APPLICATION NO. : 13/814987  
DATED : August 26, 2014  
INVENTOR(S) : Ville Takio et al.

Page 1 of 1

It is certified that error appears in the above-identified patent and that said Letters Patent is hereby corrected as shown below:

On the Title Page, Item (54) and in the Specification, Column 1, Lines 1-2 should read:

Novel 6,7-disubstituted-isoquinoline derivatives and their use

Signed and Sealed this
Tenth Day of February, 2015

Michelle K. Lee
*Deputy Director of the United States Patent and Trademark Office*